(12) United States Patent
Landegren

(10) Patent No.: US 6,558,928 B1
(45) Date of Patent: May 6, 2003

(54) ROLLING CIRCLE REPLICATION OF PADLOCK PROBES

(76) Inventor: Ulf Landegren, Uppsala University, Dept. of Medical Genetics, Biomedical Center, P.O. Box 589, Uppsala (SE), S-751 23

( * ) Notice: Subject to any disclaimer, the term of this patent is extended or adjusted under 35 U.S.C. 154(b) by 0 days.

(21) Appl. No.: 09/647,036
(22) PCT Filed: Mar. 25, 1999
(86) PCT No.: PCT/EP99/02111
§ 371 (c)(1), (2), (4) Date: Mar. 16, 2001
(87) PCT Pub. No.: WO99/49079
PCT Pub. Date: Sep. 30, 1999

(30) Foreign Application Priority Data

Mar. 25, 1998 (EP) .............................. 98302278

(51) Int. Cl.⁷ ........................ C12P 19/34; C07H 21/04
(52) U.S. Cl. ................. 435/91.1; 435/91.2; 435/7.1; 536/24.3
(58) Field of Search ............... 435/6, 7.1, 91.1, 435/91.2, 810; 536/24.3

(56) References Cited

U.S. PATENT DOCUMENTS 5,854,033 A * 12/1998 Lizardi ..................... 435/91.2

FOREIGN PATENT DOCUMENTS

WO 97/19193 * 5/1997 ............ C12Q/1/68

OTHER PUBLICATIONS

Baner et al., Nucleic Acids Res. 26(22), 5073–5078 (Nov. 15, 1998).*

* cited by examiner

Primary Examiner—Kenneth R. Horlick
(74) Attorney, Agent, or Firm—Volpe and Koenig, P.C.

(57) ABSTRACT

Rolling circle replication of a padlock primer is inhibited when it is hybridized to a target nucleic acid that is long or circular. The invention provides methods of addressing this problem including cutting the target nucleic acid near or preferably at the site which hybridizes with the padlock probe, whereby a 3'-end of the cut target nucleic acid acts as a primer for rolling circle replication of the padlock probe. Also included is a method of assaying for a polyepitopic target by the use of two affinity probes each carrying an oligonucleotide tag and of a padlock probe for rolling circle replication in association with the two affinity probes 20 Claims, 11 Drawing Sheets

| Sample | FokI | Phi29 |
|--------|------|-------|
| 1 | + | − |
| 2 | + | + |
| 3 | − | − |
| 4 | − | + |

| Sample | FokI | Phi29 |
|--------|------|-------|
| 1 | + | − |
| 2 | + | + |
| 3 | − | − |
| 4 | − | + |

| Sample | FokI | Phi29 |
|--------|------|-------|
| 1 | + | − |
| 2 | + | + |
| 3 | − | − |
| 4 | − | + |

| Sample | Ligas | FokI | Phi29 |
|--------|-------|------|-------|
| 1 | − | − | − |
| 2 | − | − | + |
| 3 | + | − | − |
| 4 | + | − | + |
| 5 | − | + | − |
| 6 | − | + | + |
| 7 | + | + | − |
| 8 | + | + | + |

M13mp18+strand circular

| Sample | Ligas | MvaI | Phi29 |
|---|---|---|---|
| 1 | − | − | − |
| 2 | − | − | + |
| 3 | + | − | − |
| 4 | + | − | + |
| 5 | − | + | − |
| 6 | − | + | + |
| 7 | + | + | − |
| 8 | + | + | + |

| Sample | Ligas | RE | HpaII |
|---|---|---|---|
| 1 | − | − | − |
| 2 | − | − | + |
| 3 | + | − | − |
| 4 | + | − | + |
| 5 | − | + | − |
| 6 | − | + | + |
| 7 | + | + | − |
| 8 | + | + | + |
| 9 | − | − | − |
| 10 | − | − | + |
| 11 | + | − | − |
| 12 | + | − | + |
| 13 | − | + | − |
| 14 | − | + | + |
| 15 | + | + | − |
| 16 | + | + | + |

Fig.14.

ROLLING CIRCLE REPLICATION OF PADLOCK PROBES

Various methods are in use for detecting single or multiple nucleotide variations in DNA or RNA samples (1,2). Most methods depend on amplification of the target sequence prior to analysis, commonly by PCR. Thereby, valuable information on the localisation of allelic variants is lost. Information on the localisation of sequence variants is important e.g. to determine haplotypes of several variable sequences along chromosomes in the study of inherited disorders; to determine if two mutations in a gene are present in the same copy or in alternate alleles; or to study replication timing of alleles in the cell cycle (3) or the distribution of mutant cells in a malignant tissue. Single nucleotide discrimination in single copy gene sequences in situ is presently not possible, but it has recently been shown to work efficiently on repeated sequences using padlock probes (4), a new class of gene diagnostic probe molecules (5). These are linear oligonucleotides with target complementary sequences at the ends and a non-target complementary sequence in between. When hybridised to the correct target DNA sequence, the two ends are brought together, head to tail, and can be joined by a DNA ligase. As a consequence of the helical nature of double stranded DNA the resulting circular probe molecule is catenated to the target DNA strand. This probe design has some important features. First, the requirement for two independent oligonucleotide hybridisation events in order for ligation to occur provides sufficient specificity to detect single-copy genes in the complexity of a complete human genome (6–8). Second, ligation is greatly inhibited by mismatches at the ligation junction, allowing single nucleotide distinction in the target sequence (4,8–10). Third as the topological link between probe and target DNA strands is independent of hybridisation stability, denaturing washes can be applied reducing non-specific hybridisation (5). Fourth, unlike PCR or LCR, only intramolecular interactions probe reactions are scored, avoiding problems of simultaneously applying large sets of probes (11). Whereas combinations of many pairs of PCR primers leads to a rapidly increasing risk of spurious amplification products, formed between any combinations of primers, this is not the case for padlock probes. Lastly, the joining of the probe ends creates a new class of molecules, not present before the reaction; these circular molecules can be amplified In a rolling circle replication reaction to detect ligated probes (12,13).

Amplification of a circular nucleic acid molecule free in solution by a rolling circle replication reaction may be achieved simply by hybridising a primer to the circular nucleic acid and providing a supply of nucleotides and a polymerase enzyme. However, problems may arise when the circular nucleic acid is not free in solution. In the particular case of a padlock primer which is catenated to its target, it might reasonably be expected that the target would inhibit a rolling circle replication reaction. In previously unpublished work leading up to the present invention, the inventors have demonstrated that such inhibition does indeed take place (18). They found that, if the target is circular, for example the circular 7 kbM13 genome, then rolling circle replication of a padlock primer catenated to the target is effectively prevented. Where a target is linear, it is possible in principle for a padlock formed thereon to slide along the target molecule and off the end, thereby becoming free in solution and available for amplification by a rolling circle replication reaction. Alternatively, the target sequence, 3' of the site of binding by the padlock probe, may be digested by exonucleolysis, allowing the remaining target strand to prime rolling circle replication. In practice, the inventors have found that this sliding and uncoupling effect is possible to a limited extent even with long linear targets. Thus, converting the circular 7 kbM13 genome by restriction at a single site into a linear 7 kb nucleic acid molecule with 3.5 kb upstream and 3.5 kb downstream of the hybridisation site of the padlock primer, limited amplification of the padlock primer was possible by rolling circle replication. But where the target nucleic acid is substantially shorter, e.g. a few tens or hundreds of bases, rolling circle replication of a padlock primer formed thereon is much more rapid and efficient.

BRIEF DESCRIPTION OF THE DRAWINGS

FIG. 14 shows four oligomers hybridized together.

THE INVENTION

Figure 1:
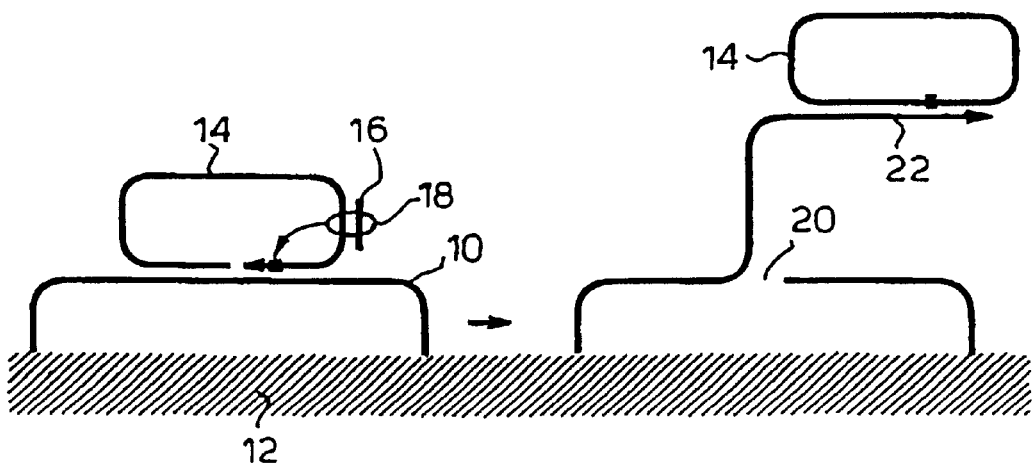
FIG. 1 shows positioning of the enzyme on the padlock probe and cutting of the target sequence in accordance with the method of the present invention.

In one aspect of the present invention, this problem is addressed by cutting the target molecule before, during or after target recognition and probe circularisation. In this aspect the invention provides a method of detecting a target sequence of a target nucleic acid which method comprises the steps of:

i) providing a padlock probe for the target sequence,
ii) forming a hybrid of the padlock probe with the target nucleic acid, and circularising the padlock probe,
iii) cutting the target nucleic acid at or near the target sequence, this step iii) being performed before, during or after step ii), and
iv) effecting rolling circle replication of the padlock probe.

The target nucleic acid may in principle be DNA or RNA. The method of the invention is likely to be useful particularly when the target nucleic acid is a long-chain or circular molecule. The target sequence is of sufficient length to hybridise with the two ends of the padlock probe. The method of the invention is expected to be particularly useful for localised detection of single-copy gene sequences and for distinction among sequence variants in microscopic specimens, and for probes immobilised in one or two dimensional arrays.

The padlock probe has a 5'-end sequence and 3'-end sequence complementary to the target sequence; so that it can be circularised e.g. by ligation when hybridised to the target sequence. Precise complementarity is not necessarily required, but there must be sufficient complementarity to permit hybridisation of the padlock probe to the target sequence, and circularisation of the padlock probe by ligation. It is in principle possible to provide a padlock probe in two parts, in which case two ligation reactions are required to achieve circularisation. The size is of the padlock probe needs to be suitable to permit amplification by a rolling circle replication reaction, preferably at least about 25 nt and not more than 150–200 nt, though larger probes are possible particularly when used with a polymerase not having exonuclease activity, especially 5' to 3' exonuclease activity.

Step ii) of the method involves forming a hybrid of the padlock probe with the target sequence of the target nucleic acid, and circularising the padlock probe. These steps may be carried out under conventional conditions. If the target nucleic acid sample under investigation does not contain the target sequence, then hybridisation and circularisation of the padlock probe occur not at all or only to a limited extent.

In step iii) of the method, the target nucleic acid is cut at or near the target sequence. This cut may be made by means well known in the art. Although the distance of the restriction site from the target sequence may be substantial, e.g. 3.5 kb as above or even greater, it is preferably within a few bases or a few tens of bases of the target sequence.

Thus the target nucleic acid may be linearised by restriction digestion before the addition of a padlock probe. Alternatively, a primer extension reaction may be performed to generate a relatively short nucleic add molecule suitable as a target for padlock probe recognition For in situ detection in metaphase chromosomes, these two methods are subject to the disadvantage that they risk causing loss of target DNA and thereby loss of detection. Preferably therefore step iii) is performed by subjecting the hybrid to restriction thereby cutting the target nucleic acid at or near the target sequence but without cutting the circularised padlock probe.

In step iv), the padlock probe is amplified by a rolling circle replication reaction. This usually requires a primer to hybridise to the circularised padlock probe, a supply of nucleotides and a polymerase enzyme, and may be effected by means well known in the art. A preferred polymerase enzyme is φ29 DNA polymerase which has high processivity and 3'-exonuclease activity.

Therefore when a target sequence is cleaved 3' of where a padlock probe has bound, then any non-basepaired nucleotides may be removed by the polymerase, until a 3' end basepaired to the padlock probe is obtained, whereupon rolling circle replication (RCR) can be initiated without the addition of an external primer, and ensuring that the RCR product is continuous with the target sequence. Such cleavage can be accomplished by hybridising an oligonucleotide to the target sequence downstream of where the probe has bound. The sequence can then be cleaved using a restriction enzyme whose recognition sequence has been rendered double stranded by this hybridisation. Alternatively, a hairpin oligonucleotide can be used, having one double stranded end containing a recognition sequence for a type IIS enzyme, e.g. FokI, and another end hybridising to the target sequence 3' of where the padlock probe has bound.

If the padlock probe hybridises to the target sequence across a restriction site, then the padlock can be protected e.g. by being modified with phosphorothioates, allowing the target sequence to be cleaved without opening the padlock.

If the target nucleic acid is RNA, and is restricted at a site now within the target sequence, then a 3'-end capable of initiating rolling circle replication of the padlock primer can be obtained by RNase H digestion.

According to a preferred method, in step iii) the target nucleic acid is cut within the target sequence. An advantage of this method is that the 3'-end of the target sequence then constitutes a primer by means of which rolling circle replication of the padlock probe may be effected in step iv). Thereby the rolling circle replication product formed is contiguous with the target sequence.

To achieve this, use is preferably made of a type IIS enzyme. (Type IIS enzymes are sometimes referred to as class. IIS enzymes or Type IV enzymes.). Type IIS restriction endonucleases are described in the literature (14,15). These enzymes interact with two discrete sites on double-stranded DNA; a recognition site which is 4–7 bp long, and a cleavage site usually 1–20 bp away from the recognition site. One such type IIS enzyme is the FokI restriction endonuclease (16,17) which recognises a double-stranded 5'-GGATG-3' site and cuts at the $9^{th}$ and $13^{th}$ nucleotides downstream from the 5'-3' and 3'-5' strands respectively. When using FokI with ssDNA and oligonucleotides, cutting is observed at the $9^{th}$ or $13^{th}$ nucleotide from the recognition site. Cutting occurs independent of whether a double stranded region between the recognition and cut sites is perfectly complementary or not.

To use a type IIS enzyme in the above method, a specially designed padlock probe is required, and this forms another aspect of the invention. In this aspect there is provided an oligonucleotide suitable for use as a padlock probe for a target nucleic acid sequence, which oligonucleotide has 5'-end and 3'-end sequences complementary to the target sequence; a first site for recognition by a type IIS enzyme; and a second site where at least one nucleotide residue and/or internucleotide bond is modified to protect the oligonucleotide from restriction by the type IIS enzyme.

The first site for recognition by the type IIS enzyme needs to be positioned on the padlock probe so that the enzyme cuts the target nucleic acid sequence. And the second site needs to be positioned on the padlock probe in relation to the first site so as to protect the padlock probe from being cut by the type IIS enzyme The relative positions of the first and second sites, in relation to the 5'-end and 3'-end sequences, depend on the particular type IIS enzyme to be used. The modification at the second site may also depend on the particular type IIS enzyme to be used. For example, when a FokI enzyme is to be used, and similarly for the type II enzyme HincII, phosphorothioate internucleotide bonds are effective to prevent cleavage of the padlock probe.

In the method of the invention, the padlock probe is hybridised to the target sequence and circularised. Then the padlock probe is made double-stranded at the first site for recognition by a type IIS enzyme. Then the enzyme is added and used to cleave the target sequence. Then conditions are adjusted to so as to cause a cleaved fragment of the target sequence to act as a primer to initiate rolling circle replication of the padlock probe. Either (or neither) of the padlock probe and the target nucleic acid may be immobilised.

The system is illustrated diagrammatically in FIG. 1 of the accompanying drawings. This shows that in the first stage, a target nucleic acid 10 has been immobilised on a support 12. A padlock probe 14 has been hybridised to a target sequence of the target nucleic acid and has been circularised. An oligonucleotide primer 16 has been hybridised to a first site of the padlock probe for recognition by a type IIS enzyme 18, which is about to cut the target nucleic acid within the target sequence. In the second stage of the figure, the type IIS restriction endonuclease has cut the target sequence at 20 and the resulting 3'-end 22 has been chain extended by a rolling circle replication reaction involving the padlock probe 14.

The alternative in which the target nucleic acid is cut before hybridisation with a probe, gives rise to another possibility. This is that the target nucleic acid fragment that results from cutting may itself be circularised and amplified by rolling circle replication. Thus in this aspect the invention provides a method of detecting a target nucleic acid having two non-adjacent target sequences, which method comprises the steps of:

i) Cutting the target nucleic acid so as to create a target nucleic acid fragment having a 5'-end target sequence and a 3'-end target sequence,
ii) Providing a probe having two adjacent sequences complementary to the target sequences,
iii) Forming a hybrid of the target nucleic acid fragment with the probe, and circularising the target nucleic acid fragment, and
iv) Effecting rolling circle replication of the circularised target nucleic acid fragment. Preferably this step is performed using the probe as primer.

If the rolling circle product is digested and the size of the monomers estimated by gel electrophoresis, then the size of the target sequence can be estimated This can be of value to estimate the size of trinucleotide repeats in conditions such as the fragile X syndrome. Alternatively, the circularised molecule or rolling circle replication products thereof can be investigated, e.g. by DNA sequence analysis. In a variant of the above, both the probe and the target nucleic acid can be designed to undergo circularisation. In this latter case, either can be opened to prime rolling circle replication of the other.

Figure 4:
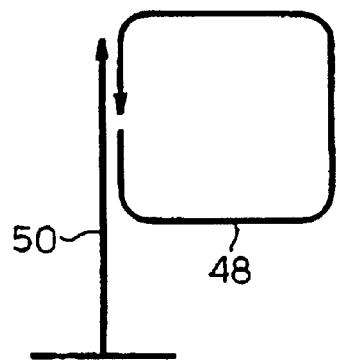
FIG. 4 shows a target nucleic acid fragment in solution that has been hybridized to an immobilized probe and circularized.

This aspect of the invention is illustrated in FIG. 4 of the accompanying drawing, in which a target nucleic acid fragment 48 in solution has hybridised to an immobilised probe 50, and has been circularised. Thereafter, the immobilised probe 50 will act as a primer for rolling circle replication of the target nucleic acid fragment 48.

In another alternative it is possible, and perhaps advantageous, to use two (or more) padlock probes instead of just one. In this aspect of the invention there Is provided a method of detecting a target sequence of a target nucleic acid, which method comprises the steps of:

i) Providing a first padlock probe having 5'-end and 3'-end sequences which are complementary to the target sequence, and an intermediate sequence,
ii) Providing a second padlock probe having 5'-end and 3'-end sequences which are complementary to the intermediate sequence of the first padlock probe,
iii) Forming a hybrid by hybridising the first padlock probe to the target nucleic acid and hybridising the second padlock probe to the first padlock probe, and circularising both padlock probes,
iv) Purifying the hybrid,
v) Subjecting the hybrid to restriction thereby cutting the first padlock probe, and
vi) Effecting rolling circle replication of the second padlock probe.

In step iii), a hybrid is formed by hybridising the first padlock probe to the target nucleic acid and hybridising the second padlock probe to the first padlock probe, and circularising both padlock probes. The techniques for performing these steps are well known in the art and may be as discussed above. Any one (or none) of the target nucleic acid, the first padlock probe or the second padlock probe may be immobilised.

Step iv) of the method involves purifying the hybrid, which may be done by means of superstringent washing, e.g. using pH, temperature or percentage formamide to denature the DNA hybrid. This step is effective to remove: any second padlock probe that has not been circularised; and any second padlock probe that has hybridised to a first padlock probe which has itself not been circularised (e.g. because it has not hybridised to a target sequence). This separation may be aided if either the target nucleic acid or the first padlock probe is immobilised on a solid support. In step v), the first padlock probe is cut, and in step vi) rolling circle replication of the second padlock probe is effected. As in the previous method, it is preferred that in step v) the first padlock probe is cut within the intermediate sequence which is hybridised to the second padlock probe, to provide a primer by means of which rolling circle replication of the second padlock probe is effected in step vi).

Cutting the first padlock probe within its intermediate sequence may be effected by the use of a type IIS restriction endonuclease as described above. Alternatively, the intermediate sequence of the first padlock probe may include modified residues that may be cleaved, such as dU-residues, susceptible to base removal by UTP glycosylase. followed by cleavage by ExoIII or alkali or heat. Since the intermediate sequence may be chosen at will, it may be designed to include a recognition sequence of any convenient restriction enzyme e.g. HincII, with the second padlock probe being protected e.g. by provision of phosphorothioate linkages.

Figure 2:
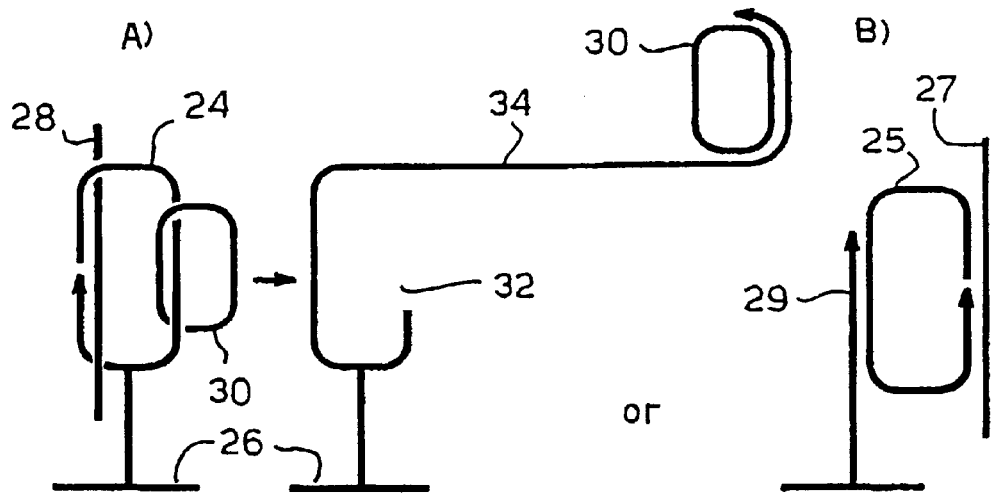
FIG. 2A shows an alternative method using two padlock probes.
FIG. 2B shows a target nucleic acid that has been hybridized to the padlock probe, which has been circularized, prior to amplification by rolling circle replication.

The system is illustrated in part A of FIG. 2. In the first part of this diagram, a hybrid has been formed by hybridising to a first padlock probe 24, which is immobilised on a solid support 26, a target sequence in solution 28, and a second padlock probe 30. Both padlock probes have been circularised. At the second stage, the first padlock probe has been cut at 32 (without cutting the second padlock probe), and the 3'-end of the restriction fragment 34 has acted as a primer for rolling circle replication of the second padlock probe.

Also included within the scope of this invention is a kit for performing the above method, which kit comprises the first padlock probe and the second padlock probe as described. In this and other cases, it will generally be convenient for the nucleotides used for rolling circle replication to include a labelled nucleotide for easy detection. Alternatively, the rolling circle replication product can be investigated using a hybridisation probe.

In FIG. 2B, a target nucleic acid fragment 27 has hybridised to the padlock probe 25. The padlock probe has been circularised and is about to be amplified by rolling circle replication using an immobilised oligonucleotide 29 as primer. In a development of this technique, both the padlock probe 25 and the target nucleic acid fragment 27 can be circularised and thus catenated if the 5'- and 3'-ends of each molecule can hybridise to the other, but in such a way that the ends to be joined by ligation do not hybridise immediately opposite one another. This probe target configuration offers increased specificity of detection; but rolling circle replication of one molecule requires linearisation of the other, preferably within the base-paired region.

Patent specification WO 96/14406 describes enzymatic synthesis of padlock probes. These probes can also be detected via a rolling circle mechanism if catenation can be avoided. This can be achieved if they are first generated with a type IIS restriction enzyme and the 5'-phosphate replaced with a thiophosphate by phosphatase treatment, followed by kinasing with γ-thiophosphate ATP. In this manner these probes are also protected from digestion with the same IIS enzyme after target recognition as described above. Binding of such enzymatically prepared probes can also be visualised using a linked detection padlock probe as also described above.

According to patent specification WO 97/00446, enhanced immune detection can be achieved by requiring coincident binding of two or more affinity probes, for example antibodies, to a target molecule. Upon target recognition, oligonucleotides bound to the affinity probes are brought close enough to be joined by ligation forming a longer oligonucleotide which can template an expotential nucleic acid amplification reaction through PCR or NASBA, etc. In this aspect, the present invention uses a related approach but employing rolling circle replication of a padlock probe. Thus the invention provides a method of assaying for a polyepitopic target by providing:

a) A first affinity probe for the target which first affinity probe carries a polynucleotide chain including a first polynucleotide sequence,
b) A second affinity probe for the target which second affinity probe carries a polynucleotide chain including a terminal second polynucleotide sequence, and
c) A padlock probe having 5'-end and 3'-end sequences which are complementary to the first polynucleotide sequence, and an intermediate sequence which is complementary to a 3'-end of the second polynucleotide sequence, which method comprises binding the first affinity probe to the target; binding the second affinity probe to the target; hybridising the padlock probe to the first polynucleotide sequence and to the second polynucleotide sequence; circularising the padlock probe; and using the second polynucleotide sequence as a primer to effect rolling circle amplification of the padlock probe.

The invention also provides a kit for performing the method, which kit comprises the first and second affinity probes and the padlock probe. Preferably the first affinity probe and the second affinity probe are selected from: polyclonal, monoclonal and single chain antibodies and fragments thereof, receptors, lectins and nucleic acid aptamers.

In the method, the first affinity probe and the second affinity probe are incubated with the target, under conditions to cause them to bind to the target. Then the padlock probe is hybridised to the first polynucleotide sequence and is circularised. If the two affinity probes bound to the target are close enough together, then the terminal second polynucleotide sequence of the second affinity probe becomes hybridised to the intermediate sequence of the padlock probe. On addition of a supply of nucleotides and a polymerase enzyme, rolling circle replication of the padlock probe can be effected. Use of a radioactively or otherwise labelled nucleotide provides a correspondingly amplified signal related to the presence or concentration of the polyepitopic target.

Figure 3:
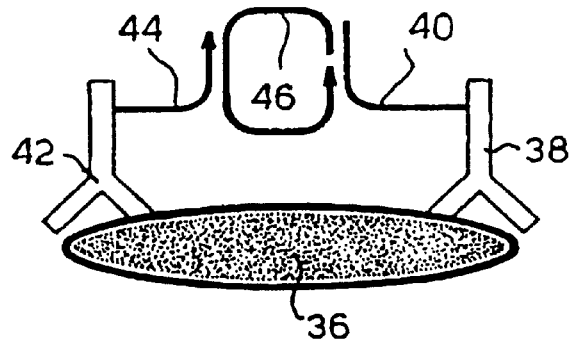
FIG. 3 shows a kit used to perform the method of the present invention, including two affinity probes.

The system is illustrated in FIG. 3 of the accompanying drawings, in which there is shown a polyepitopic target 36, a first antibody 38 for the target which carries a polynucleotide chain 40 including a first polynucleotide sequence; a second antibody 42 for the target which carries a polynucleotide chain 44 including a terminal second polynucleotide sequence; and a padlock probe 46 which has hybridised to both polynucleotide chains and has been circularised. Upon addition of a supply of nucleotides and a polymerase enzyme, the polynucleotide chain 44 will act as a primer for rolling circle replication of the padlock probe 46

Rolling circle products generated by any of the methods described herein can be visualised during synthesis using so called molecular beacons. (S Tyagi and F R Kramer, 1996, Nature Biotechnology, 14, 303–308). A molecular beacon is a usually hairpin shaped oligonucleotide carrying a fluorescing label at one end, and at the other end a compound that modulates or inhibits the fluorescence. Unfolding the normally hairpin-shaped molecular beacon modulates or enhances the fluorescence signal in an easily observed way. A molecular beacon designed to have a sequence corresponding to that of a padlock probe, can be used to monitor rolling circle replication of the padlock probe.

Figure 5:
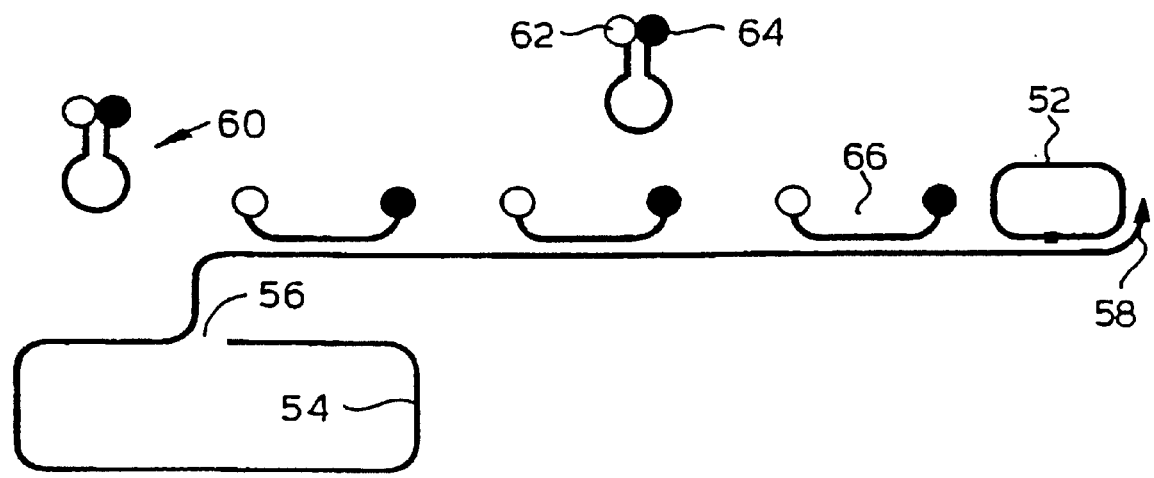
FIG. 5 shows rolling circle products generated by any one of the disclosed methods during synthesis using molecular beacons.

This system is illustrated in FIG. 5 of the accompanying drawings. A padlock probe 52 has been hybridised to a target sequence of a target nucleic acid 54 and has been circularised. The target nucleic acid has been cut at 56 and the resulting 3'-end 58 has been chain extended by a rolling circle replication reaction involving the padlock probe 52. A molecular beacon 60 has a terminal fluorescent group 62 and a terminal quenching group 64, and an intermediate sequence corresponding to that of the padlock probe 52. As rolling circle replication takes place, successive molecules of the molecular beacon become hybridised to the extending chain at 66 in a conformation which permits enhanced fluorescence of the fluorescent group.

Reference is directed to FIGS. 6–14, which are described in the following.

Experimental Section

Materials and Method

Oligonucleotides Synthesised by Interactiva

M13-Fo1s (56 nt) contains 6 phosphorothioates
M13-Fo2 (56 nt) contains no phosphorothioates
M13-Ls1 (23 nt) contains FokI cleavage-site
M13-T3s is used as template
M13-K1 (34 nt) is used as a FokI cleavage adapter.

Oligonucleotides Synthesised in House Using an ABI 394 DNA Synthesiser

M13c70-ro1 (70 nt) used as a padlock probe
Primer Mavl (21 nt) used for M13 cleavage by Mavl.
RvRo1cpr (21 nt) used for cleavage of RCR-product by HpaII.

Labelling

The probes were 5'-radiolabelled using 30 units T4 polynucleotide kinase (Amersham) in 50 μl 10 mM Tris Ac pH 7.5, 10 mM MgAc$_2$, 50 mM KAc and 30 μCi gamma 32P-ATP (3000 mCi/mMol, NEN Dupont) at 37° C. for 10 min, and the oligonucleotides were purified on a Sephadex G-50 μspin column (Pharmacia).

FokI Cleavage Using Oligonucleotides

Oligonucleotides, one labelled at the time, were mixed and allowed to hybridise by incubating 1 pmol M13-T3S, 2 pmol M13-Fo1s or M13-Fo2 together with 3 pmol M13-Ls1 or M13-K1 in 20 μl 10 mM TrisAc pH 7.5, 10 mM MgAc$_2$, 50 mM KAc, 1 mM ATP, 0.1 μg/μl BSA at 65° C. for 10 min and allowed to cool at room temperature for 10 min. FokI was added to a conc of 0.5 units/μl and the reaction was incubated at 37° C. for 60 min. The enzyme was heat inactivated at 65° C. for 20 min and the reaction was allowed to cool to room temperature for 10 min.

FokI Cleavages of M13 Using Padlock and FokI-adapter 0.75 pmol M13mp18+strand (Pharmacia), 0.25 pmol M13c70-Ro1 (labelled) and 1.5 pmol M13-K1 were mixed and allowed to hybridise as described above. The FokI cleaved was performed as described above.

Mavl Cleavages of M13 Using Padlock and Mavl-primer 0.75 pmol M13 mp18+strand (Pharmacia), 0.25 pmol M13 c70-Ro1 (labelled) and 1.5 pmol Mavl-primer in 20 μl 10 mM TrisAc pH 7.5, 10 mM MgAc$_2$, 50 mM KAc, 1 mM ATP, 0.2 μg/μl BSA was incubated at 65° C. for 10 min and allowed to cool at room temperature for 10 min. 2 units Mavl was added and the reaction was incubated at 37° C. for 60 min. the enzyme was heat-inactivated at 65° C. for 15 min and the reaction was allowed to cool to room temperature for 10 min.

Phi 29 DNA Polymerase Reaction

1 µl enzyme reaction was added to 50 mM Tris-HCl pH 7.5, 10 mM MgCl$_2$, 20mM (NH$_4$)$_2$SO$_4$, 1 mM dithiothreitol and 0.2 µg/µl BSA, 0.25 mM dNTP, 5 µCi alpha 32P dCTP (3000 Ci/mmol, NEN Dupont) and 2 µg/µl Phi29 DNA polymerase (provided from Amersham) and incubated at 37° C. for 60 min. The enzyme was heat inactivated at 65° C. for 20 min.

Cleavages of RCR-product

1 µl RCR-reaction is added in 10 mM Bis Tris Propane-HCl, 10 mM MgCl$_2$, 1 mM dithiothreitol (pH 7.0) and 1 pmol/µl RvRo1cpr and is incubated at 65° C. for 10 min and allowed to cool at room temperature for 10 min. 1 units HpaII was added and the reaction was incubated at 37° C. overnight. The enzyme was heat inactivated at 65° C. for 20 min.

Sequences

M13-Fo1s (SEQ ID NO: 1)
    CAGCA<u>GGATG</u>TCTTCTAGT$_S$G$_S$C$_S$C$_S$A$_S$A$_S$GCTTGC ATGCCTGCAGGTCGACTCTAGAGGAT

M13-Fo2 (SEQ ID NO: 2)
    CAGCA<u>GGATG</u>CCTTCTAGTGCCAAGCTTGCATG CCTGCAGGTCGACTCTAGAGGAT

M13-Ls1 (SEQ ID NO: 3)
    AGAAGACATCCTG$_S$C$_S$T$_S$G$_S$T$_S$T$_S$T$_S$T$_S$T$_S$T$_S$T$_S$

M13-T3s (SEQ ID NO: 4)
    ATCCTCTAGAGTCGACCTGCAGGCATGCAAGCT$_1$ TGGCACTGGC$_1$CGTCGTTTTACCAAACTC$_S$A$_S$A$_S$ G$_S$A$_S$A$_S$G$_S$G$_S$A$_S$C$_S$C

M13-K1 (SEQ ID NO: 5)
    CA<u>CATCC</u>GTGCAC GG<u>ATG</u>TGGTAAAAC$_1$GACGGCC

M13c70-ro1 (SEQ ID NO: 6)
    T G C C T G C A G G T C G A C T T T T T T T T T AT-G T T A A G T G A C C G G C A G C A T T T T T T T-TAGTGCCAAGCTTGCA

Primer Mav1 (SEQ ID NO: 7)
    TGGGTAACGCCAGGGTTTTCC

RvRo1cpr (SEQ ID NO: 8)
    ATGTTAAGTTGACCGGCAGCA

EXAMPLE 1

Figure 6:
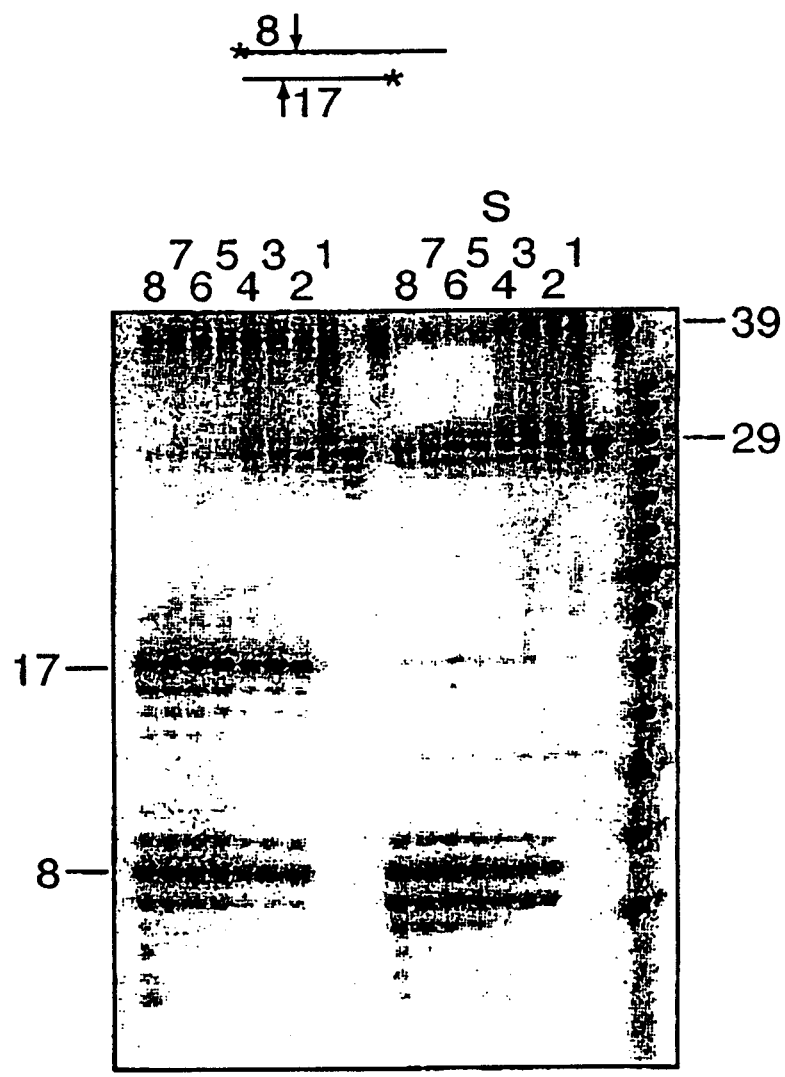
FIGS. 6–13 show the results of Examples 1 through 8, respectively.

Strand Specific Cleavage by FokI and Protection by Phosphorothioates (FIG. 6)

Enzyme titration. This experiment involves two partially complementary oligonucleotides, 29 and 39 nucleotides in length. Both were labelled at the 5' end by kinaselng, adding a 32P residue. In the left hand set 1 through 8, both oligonucleotides were composed of regular nucleotides, and addition of the type IIS restriction endonuclease FokI, resulted in cleavage of both strands. This results in loss of the 29-mer, and gain of a 17-mer fragment. Similarly, the 39-mer is replaced by an 8-mer. In the right-hand set 1 through 8, the 29-mer contained a phosphorothioate-residue where the restriction enzyme otherwise would have cleaved. The experiment shows that phosphorothioate-residues block cleavage of the modified strand without inhibiting cleavage of the other strand. (This property has not been previously demonstrated for this enzyme, but it is well established for several type II enzymes, having cleavage sites within their recognition sequence.).

EXAMPLE 2

Figure 7:
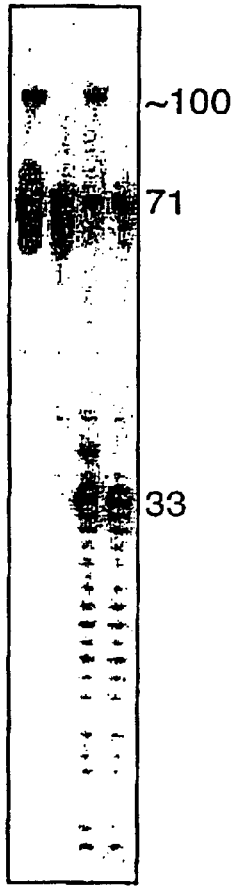
Figure 7:
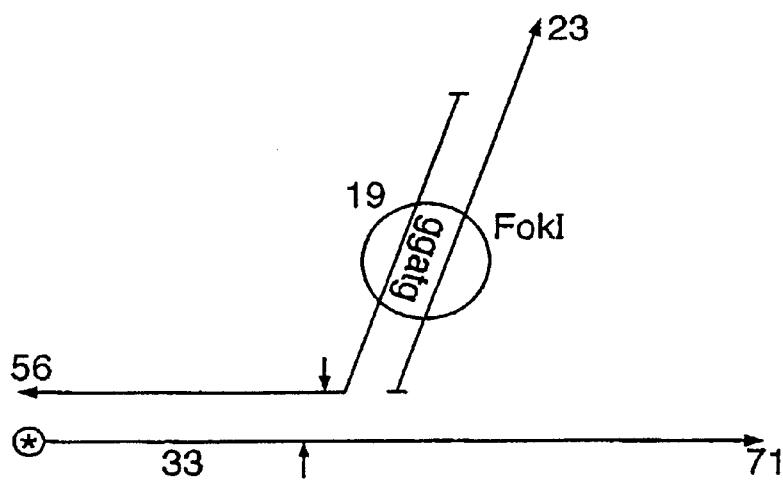

Strand-specific Cleavage Using FokI Followed by Phi29 Polymerisation (FIG. 7)

Here a branched substrate for restriction digestion was used. The 56-mer is complementary to a 23-mer at its 5'-end and to a (radiolabelled) 71-mer at its 3' end. The 23-mer includes the recognition sequence of the enzyme FokI, but is cleavage site is located across the branch. The sample shown in lane 3 is untreated. The sample in lane 1 was treated with the restriction enzyme, generating a shorter fragment of 33. In lane 4 the polymerase Phi29 and nucleotides had been present, with no consequences, compared to lane 3, as expected. Finally, in lane 2 restriction was followed by polymerisation. Only a small fraction of the cleavage products have been extended by a few nucleotides to fill in the 5' overhang generated by restriction cleavage. The experiment demonstrates that cleavage across a branch is possible, as has been previously shown by Szybalski. The reason for the poor polymerisation in this experiment, as required to initiate a rolling circle replication, is not clear (The 100 nt fragment is an unintended extension product of the 71-mer.).

EXAMPLE 3

Figure 8:
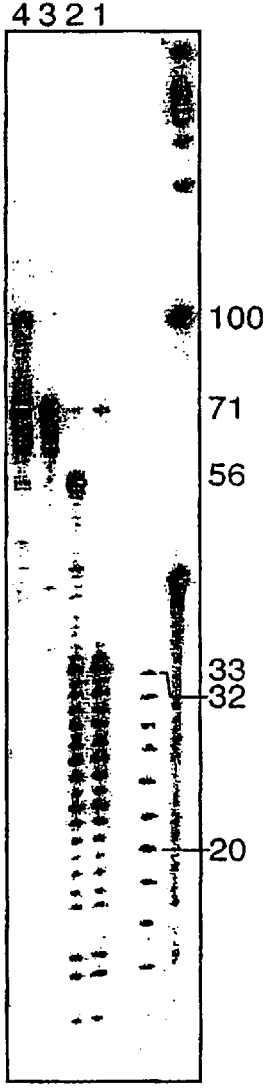
Figure 8:
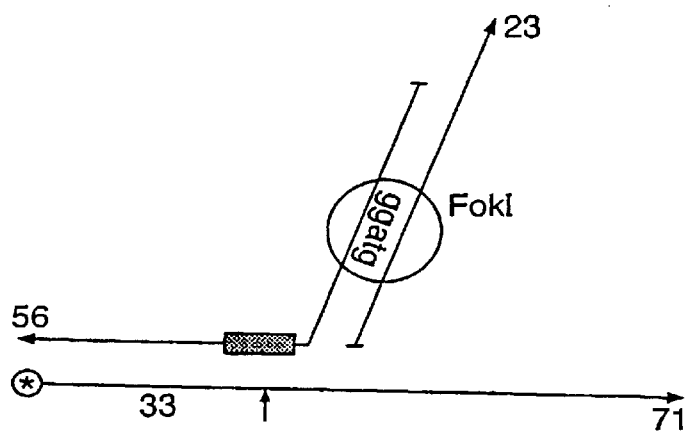

Strand-specific Cleavage Using FokI and Protection by Phosphorothioates Followed by Phi29 Polymerisation (FIG. 8)

The experiment is similar to the previous one, except that in this experiment the 56-mer was protected from restriction cleavage by being modified with phosphorothioates. Lane 3: starting material Lane 1: restriction cleaved. Lane 4: Addition of polymerase and nucleotides; most 56-mers remain unchanged (although some seem to have been extended somehow as mentioned for the above experiment). Lane 2: Here most of the 33-mer cleavage products have been extended, copying the now uncleaved 56-mer, just as would be required to initiate a rolling circle replication by directing a cleavage reaction to the target strand for padlock recognition, allowing the target to prime a rolling-circle replication reaction.

EXAMPLE 4

Figure 9:
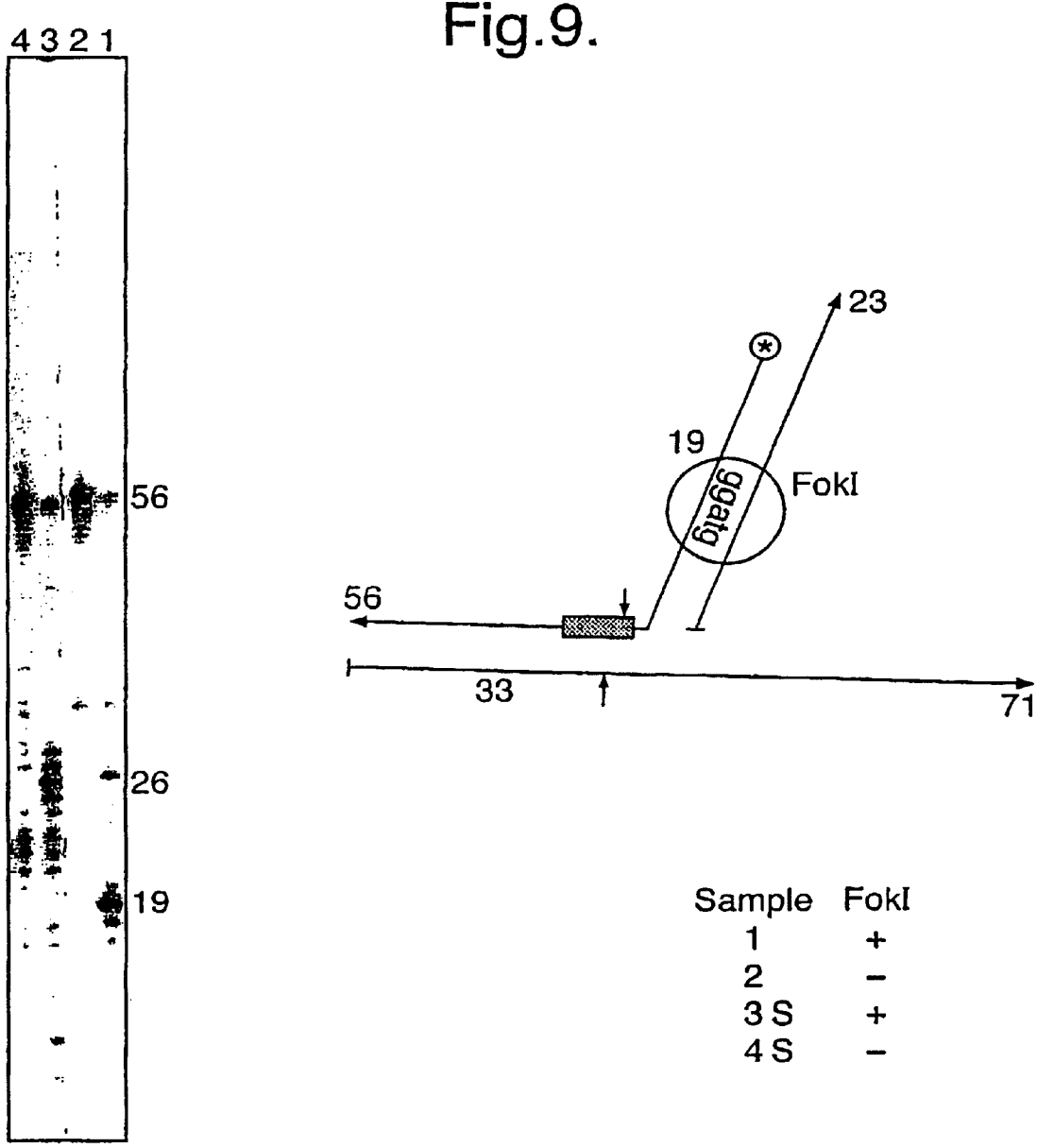

Strand-specific Cleavage by FokI and Protection by Phosphorothioates (FIG. 9)

A simpler variant of the preceding experiment, but with the 56-mer strand 5' labelled with radioactive phosphate. The unprotected strand is cleaved as expected, but the protected one is cleaved farther away than normal, where it is unprotected, indicating that a larger sequence may have to be protected by being modified with phosphorothioates.

EXAMPLE 5

Figure 10:
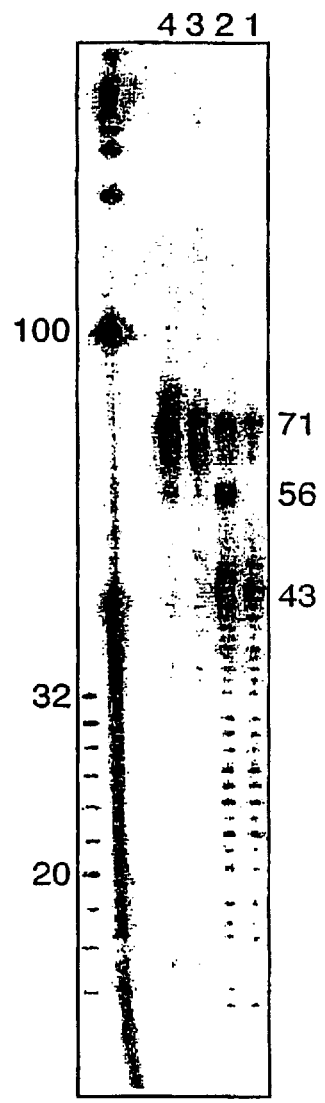
Figure 10:
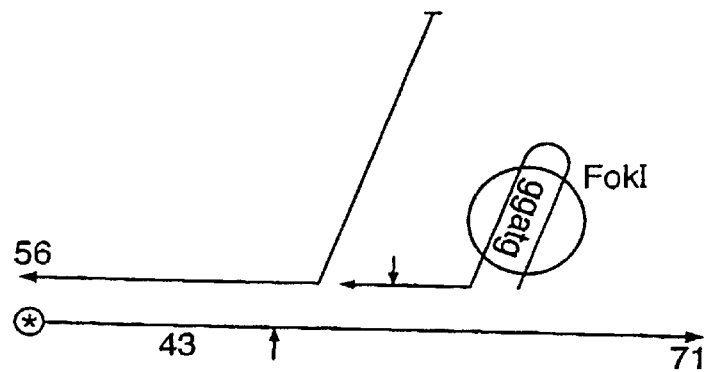

Cleavage by FokI by Using a FokI-adapter (FIG. 10)

In this experiment an alternative means is used to cleave the padlock-target strand, in this case downstream of where the probe has bound. An oligonucleotide that includes a self-complementary segment directs recognition by the restriction enzyme and cleavage where this adapter hybridises to a target strand. Lane 3: no restriction enzyme. Lane 1: restriction resulting in a shorter fragment of 43 bases Lane 4: no effect by addition of polymerase. Lane 2, some of the 43-mer cleavage product is extended by the polymerase to generate a 56-mer, templated by the unlabelled 56-mer oligonucleotide.

EXAMPLE 6

Figure 11:
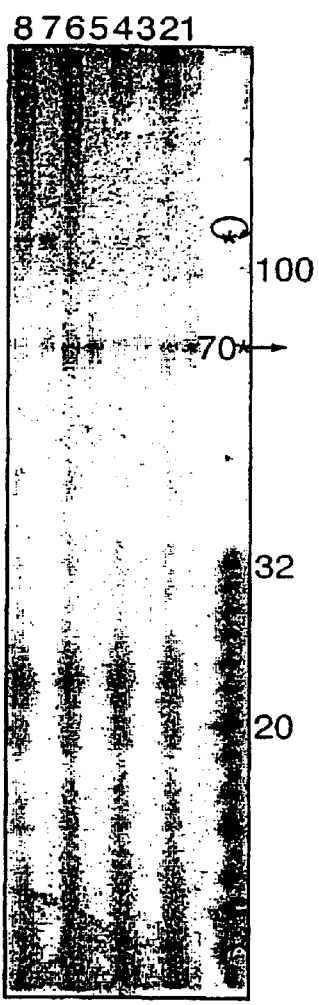
Figure 11:
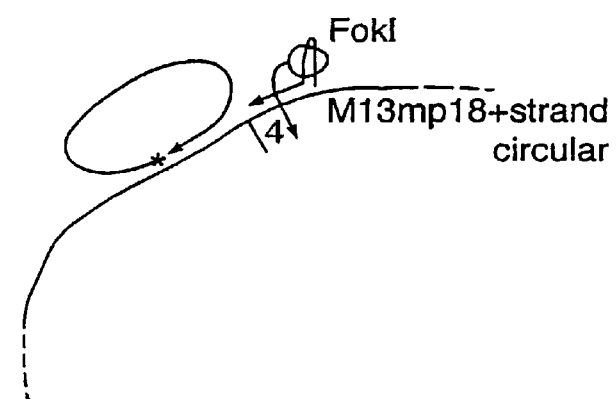

Initiation of Rolling Circle Replication by Cleavage of the Target Strand (FIG. 11)

In this experiment the external adapter of the previous experiment was used to cleave the circular single stranded M13 target for recognition by a padlock probe. Labelling was by incorporation of radioactive nucleotides, and with a 5'-labelled padlock probe. This experiment as shown here is not conclusive because unligated padlocks can prime a rolling-circle replication, templated by M13. This is addressed in the gel shown in Example 8.

Figure 12:
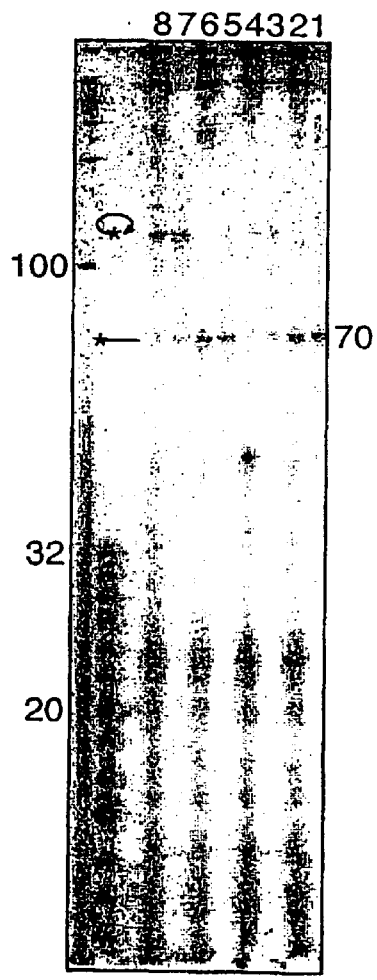
Figure 12:
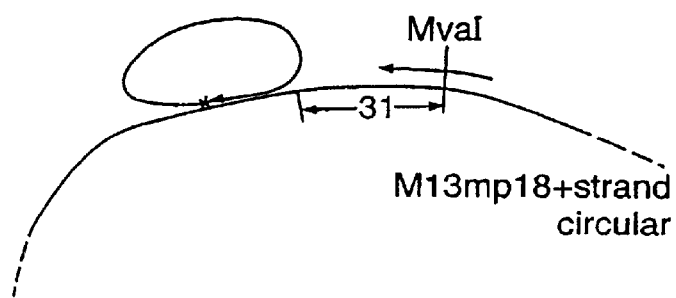

EXAMPLE 7
Initiation of Rolling Circle Replication by Cleavage of the Target Strand (FIG. 12)

Similar to the preceding experiment except that cleavage of the target strand took advantage of a resident restriction site which was rendered double stranded by hybridising an oligonucleotide. Again the two types of polymerised molecules are distinguished in Example 8.

Figure 13:
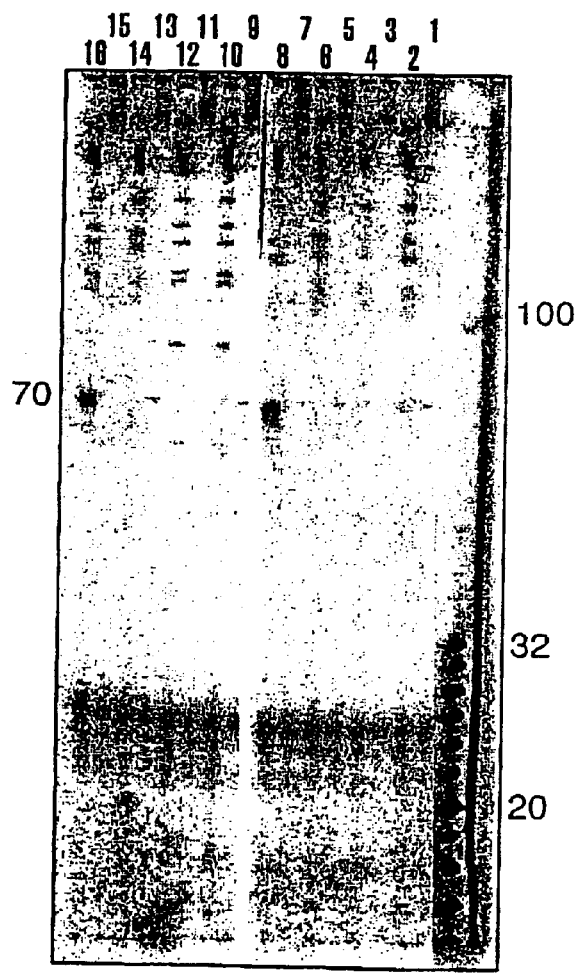

EXAMPLE 8
Cleavage of Rolling Circle Product with Restriction Enzyme (FIG. 13)

Here the experiments shown in Examples 6 and 7 have been further investigated, to reveal that the polymerase Phi29 can effect a rolling-circle replication of the circularised padlock probes, and that the reaction was primed by the target sequence after the target M13 strand was cleaved using a FokI adapter (Example 6) or the resident recognition sequence for Mavl. Ligase indicates whether the padlock probe has been ligated. RE means either FokI (lanes 1–8) or Mavl (lanes 9–16), used as a means to cleave the target molecule downstream of the site where the padlock probe has bound. All samples were treated with Phi29 polymerase. Products of the extension reaction shown in even-number lanes were treated with the restriction enzyme HpaII in the presence of oligonucleotide RvRo1cpr to cleave the rolling-circle products to monomers. The cleavage allowed identification of polymerisation products that arise by copying of the circularised padlock probe, as opposed to ones templated by the M13 genome. The 70-mer product of the enzyme reaction which is visible in lanes 8 and 16 clearly shows that a rolling circle replication was primed from the target strand by cleaving the M13 molecule that served as target for ligation, downstream of where the padlock probe had bound. This reaction generated copies of the padlock probe.

Figure 14:
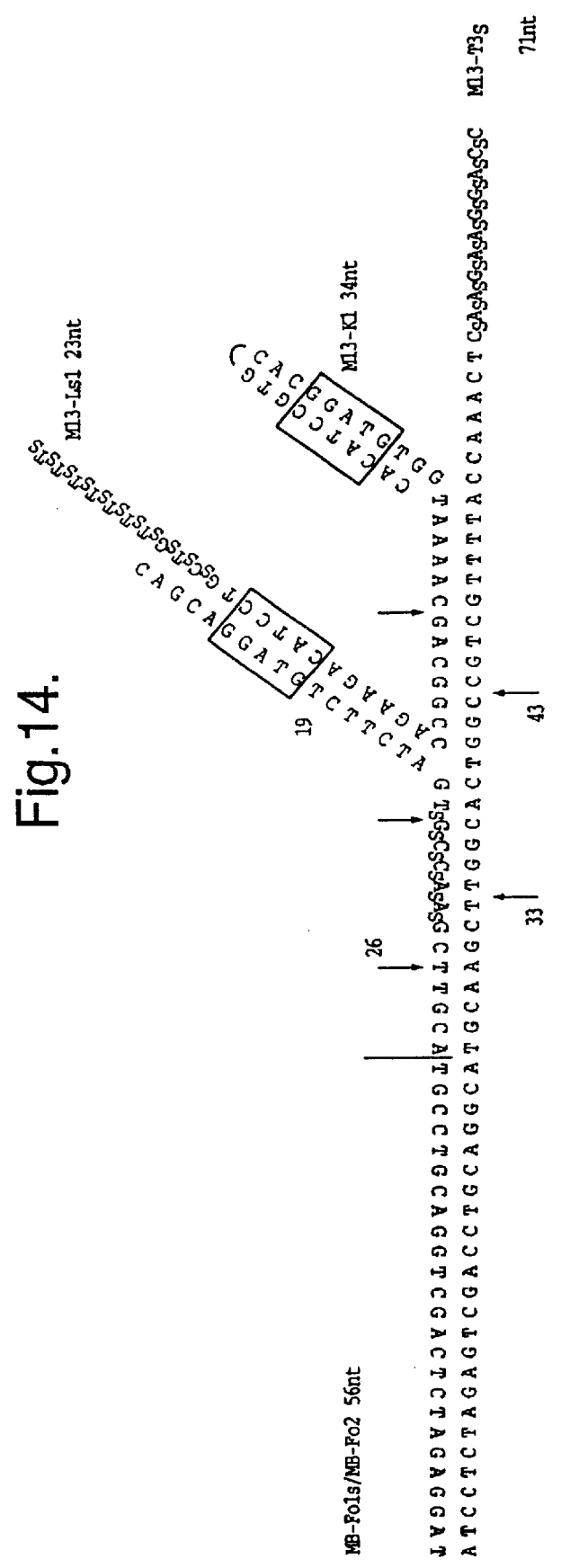

FIG. 14 shows the four oligomers M13-Fo1s (56 nt); M13-Ls1 (23 nt); M13-K1 (34 nt) and M13-T3s (71 nt) hybridised together. Sites for Fok1 binding and cleavage, and phosphorothioate bonds, are shown together with oligonucleotide lengths.

REFERENCES

1. Syvänen, A-C and Landegren, U (1994) *Hum. Mutat.* 3, 172–179.
2. Landegren, U (1996) Laboratory protocols for mutation detection, Oxford University Press, Oxford, UK.
3. Knoll, J H M, Cheng, S-D and Lelande, M (1994) *Nature Genetics*, 6, 41–46.
4. Nilsson, M, Krejci, K. Koch, J, Kwiatkowski, M, Gustavsson, P and Landegren U (1997) *Nature Genet.* 16, 252–255.
5. Nilsson, M, Malmgren H, Samiotaki, M, Kwiatkowski, M, Chowdhary, B P and Landegren U (1994) *Science*, 265, 2085–2088.
6. Saiki, R K, Scharf, F A, Faloona, F A, Mullis, C T, Horn, H A, Erlich, H A and Arnheim, N (1985) *Science*, 230, 1350–1354.
7. Barany, F (1991) *Proc. Natl. Acad. Sci, USA*, 88, 189–193.
8. Landegren, U., Kaiser, R, Sanders, J and Hood, L (1988) *Science*, 241, 1077–1080.
9. Wu, D Y and Wallace, R B (1989) *Gene*, 76, 245–254.
10. Lou, J, Bergstrom, D, E and Barany, F (1996) *Nucleic Acids Res.*, 24, 3071–3078.
11. Landegren, U and Nilsson, M, (1998) *Annals Med*, In press.
12. Fire, A and Xu, S-Q (1995) *Proc. Natl. Acad. Sci. USA*, 92, 4641–4645.
13. Liu, D, Daubendiek, S L, Zillman, M A, Ryan, K and Kool, E T (1996) *J. Am. Chem. Soc.*, 118, 1587–1594.
14. Szybalski, W (1985) *Gene*, 40, 169–173.
15. Szybalski, W et al (1991), *Gene*, 100, 13–26.
16. Podhajska, A J and Szybalski, W (1985) *Gene*, 40, 175–182.
17. Kim, S C et al (1996), *J. Mol. Biol.*, 258, 638–649.
18. Banér, J et al (1998), *N. Acids Res.*, 26, 5073–8.

---

What is claimed is:

1. A method comprising:
   i) providing a padlock probe for the target sequence,
   ii) forming a hybrid of the padlock probe with the target nucleic acid, and circularizing the padlock probe,
   iii) cutting the target nucleic acid at or near the target sequence, this step iii) being performed before, during or after step ii), and
   iv) effecting rolling circle replication of the padlock probe.

2. The method of claim 1, wherein step iii) is performed by subjecting the hybrid to restriction thereby cutting the target nucleic acid at or near the target sequence but without cutting the circularised padlock probe.

3. The method of claim 1, wherein in step iii) the target nucleic acid is cut within the target sequence to provide a primer by means of which rolling circle replication of the padlock probe is effected in step iv).

4. The method of claim 1, wherein the target nucleic acid is cut downstream of the target sequence following which any non-basepaired nucleotides are removed by a 3'-exonuclease.

5. The method of claim 4, wherein Phi29 is used as a polymnerase enzyme having also 3'-exonuclease activity.

6. The method of claim 3, wherein in step iii) restriction is effected by means of a type IIS enzyme.

7. The method claim 1, wherein the target nucleic acid is circular.

8. An oligonucleotide suitable for use as a padlock probe for a target nucleic acid sequence, which oligonucleotide has 5'-end and 3'-end sequences complementary to the target sequence; a first site for recognition by a type IIS enzyme; and a second site where at least one nucleotide residue and/or interucleotide bond is modified to protect the oligonucleotide from restriction by the type IIS enzyme.

9. The oligonucleotide of claim 8, wherein at least one phosphorothioate interucleotide bond is provided at the second site to protect the oligonucleotide from restriction by the type IIS enzyme.

10. The oligonucleotide of claim 8, wherein the first site is suitable for recognition by a type IIS enzyme FokI.

11. A method comprising:
   i) cutting the target nucleic acid so as to create a target nucleic acid fragment having a 5'-end target sequence and a 8'-end target sequence,
   ii) providing a probe having two adjacent sequences complementary to the two target sequences,
   iii) forming a hybrid of the target nucleic acid fragment with the probe, and circularising the target nucleic acid fragment, and
   iv) effecting rolling circle replication of the circularised target nucleic acid fragment.

12. A method comprising:
   i) providing a first padlock probe having 5'-end and 8'-end sequences which are complementary to the target sequence, and an intermediate sequence,
   ii) providing a second padlock probe having 5'-end and 8'-end sequences which are complementary to the intermediate sequence of the first padlock probe,
   iii) forming a hybrid by hybridising the first padlock probe to the target nucleic acid and hybridising the second padlock probe to the first padlock probe, and circularising both padlock probes,
   iv) purifying the hybrid,
   v) subjecting the hybrid to restriction thereby cutting the first padlock probe, and
   vi) effecting rolling circle replication of the second padlock.

13. The method of claim 12, wherein in step v) the first padlock probe is cut within the intermediate sequence which has hybridised to the second padlock probe, to provide a primer by means of which rolling circle replication of the second padlock probe is effected in step vi).

14. The method of claim 12, wherein in step v) the first padlock probe is cut downstream of the intermediate sequence which has hybridised to the second padlock probe, following which any non-basepaired nucleotides are removed by a 3'-exonuclease to provide a primer by means of which rolling circle replication of the second padlock probe is effected in step vi).

15. The method of claim 14, wherein Phi29 is used as a polymerase enzyme having also 3'-exonuclease activity.

16. The method of 13, wherein in step v) restriction is effected by means of a type IIS enzyme.

17. A kit for detecting a target sequence of a target nucleic acid, which kit comprises:
   a) a first padlock probe having 5'-end and 3'-end sequences which are complementary to the target sequence, and an intermediate sequence, and
   b) a second padlock probe having 5'-end and 3'-end sequences which are complementary to the intermediate sequence of the first probe.

18. A kit for assaying for a polyepitopic target which kit comprises:
   a) a first affinity probe for the target which first affinity probe carries a polynucleotide chain including a first polynucleotide sequence,
   b) a second affinity probe for the target which second affinity probe carries a polynucleotide chain including a terminal second polynucleotide sequence, and
   c) a padlock probe having 5'-end and 3'-end sequences which are complementary to the first polynucleotide sequence, and an intermediate sequence which is complementary to the second polynucleotide sequence.

19. The kit of claim 18, wherein the first affinity probe and the second affinity probe are both antibodies.

20. A method comprising:
   providing a first affinity probe for the target which first affinity probe carries a polynucleotide chain including a first polynucleotide sequence, a second affinity probe for the target which second affinity probe carries a polynucleotide chain including a terminal second polynucleotide sequence, a padlock probe having 5'-end and 3'-end sequences which are complementary to the first polynucleotide sequence, and an intermediate sequence which is complementary to the second polynucleotide sequence;
   binding the first affinity probe to the target;
   binding the second affinity probe to the target;
   hybridising the padlock probe to the first polynucleotide sequence and to the second polynucleotide sequence;
   circularising the padlock probe; and
   using the second polynucleotide sequence as a primer to effect rolling circle amplification of the padlock probe.

* * * * *

UNITED STATES PATENT AND TRADEMARK OFFICE
CERTIFICATE OF CORRECTION

PATENT NO. : 6,558,928 B1  Page 1 of 1
APPLICATION NO. : 09/647036
DATED : May 6, 2003
INVENTOR(S) : Ulf Landegren It is certified that error appears in the above-identified patent and that said Letters Patent is hereby corrected as shown below:

In Column 15, Line 44, in Claim 11, delete "8" and insert --3--.

In Column 15, Line 53, in Claim 12, delete "8" and insert --3--.

In Column 15, Line 57, in Claim 12, delete "8" and insert --3--.

Signed and Sealed this

Fourth Day of November, 2008

JON W. DUDAS
*Director of the United States Patent and Trademark Office*

SEQUENCE LISTING

<160> NUMBER OF SEQ ID NOS: 8

<210> SEQ ID NO 1
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide M13- Fo1s

<400> SEQUENCE: 1
cagcaggatg tcttctagtg ccaagcttgc atgcctgcag gtcgactcta gaggat        56

<210> SEQ ID NO 2
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide M13-Fo2

<400> SEQUENCE: 2
cagcaggatg ccttctagtg ccaagcttgc atgcctgcag gtcgactcta gaggat        56

<210> SEQ ID NO 3
<211> LENGTH: 23

```
<212> TYPE: DNA
<213> ORGANISM: Artificial Sequence
<220> FEATURE:
<223> OTHER INFORMATION: Description of Artificial Sequence:
      Oligonucleotide M13-Ls1

<400> SEQUENCE: 3
agaagacatc ctgctgtttt ttt                                              23

<210> SEQ ID NO 4
<211> LENGTH: 71
<212> TYPE: DNA
<213> ORGANISM: Artificial Sequence
<220> FEATURE:
<223> OTHER INFORMATION: Description of Artificial Sequence:
      Oligonucleotide M13-T3s

<400> SEQUENCE: 4
atcctctaga gtcgacctgc aggcatgcaa gcttggcact ggccgtcgtt ttaccaaact      60
caagaaggac c                                                           71

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide M13-K1

<400> SEQUENCE: 5
cacatccgtg cacggatgtg gtaaaacgac ggcc                                  34

<210> SEQ ID NO 6
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide M13c70-ro1

<400> SEQUENCE: 6
tgcctgcagg tcgactttt tttttatgtt aagtgaccgg cagcattttt tttttagtgc       60
caagcttgca                                                             70

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Primer
      MvaI

<400> SEQUENCE: 7
tgggtaacgc cagggttttc c                                                21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide RvRo1cpr

<400> SEQUENCE: 8
atgttaagtt gaccggcagc a                                                21
```